*US006881570B1*

(12) United States Patent
Akimoto (10) Patent No.: US 6,881,570 B1
(45) Date of Patent: Apr. 19, 2005

(54) TEST PIECE AND QUANTITATIVE METHOD AND APPARATUS FOR AN ORGANISM-ORIENTED SUBSTANCE

(75) Inventor: Taizo Akimoto, Kaisei-machi (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 0 days.

(21) Appl. No.: 09/461,308

(22) Filed: Dec. 15, 1999

(30) Foreign Application Priority Data

Dec. 15, 1998 (JP) .......................................... 10-356817

(51) Int. Cl.$^7$ ............................. C12M 1/34; C12Q 1/68; C12P 19/34; C07H 21/02; C07H 21/04
(52) U.S. Cl. ........................ 435/287.2; 435/6; 435/91.1; 435/287.1; 536/23.1; 536/24.3; 536/24.33
(58) Field of Search ........................ 435/6, 91.1, 91.2, 435/183, 283.1, 287.1, 287.2; 436/501, 94; 536/23.1, 24.3, 24.33, 25.3, 25.32

(56) References Cited

U.S. PATENT DOCUMENTS

| | | | | |
|---|---|---|---|---|
| 5,631,734 A | * | 5/1997 | Stern et al. | .................. 356/317 |
| 5,807,522 A | * | 9/1998 | Brown et al. | .................. 422/50 |
| 5,849,290 A | * | 12/1998 | Brown et al. | .............. 424/94.4 |
| 5,974,164 A | * | 10/1999 | Chee | ........................... 382/129 |

FOREIGN PATENT DOCUMENTS

| | | | | |
|---|---|---|---|---|
| JP | 5-20712 | | 3/1993 | ............. G01T/1/29 |
| SE | 9703251-0 | * | 4/1999 | |

OTHER PUBLICATIONS

Arnold et al., Phosphorylation of the human estrogen receptor on tyrosine 537 in vivo and by Src family tyrosine kinases in vitro, Mol. Endocrinol. 9, 24–33, 1995.*

Larin et al., Fluorescence in situ hybridization of multiple probes on a standard glass microscope slide. Nucleic Acids Res. 22, 3689–3692. 1994.*

Cardullo et al., Detection of nucleic acid hybridization by nonradiative fluorescence resonance energy transfer. Proc. Natl .Acad. Sci. USA, 85, 8790–9794, 1988.*

Pastore et al., A quantitative polymerase chain reaction (PCR) assay completely discriminates between Duchenne and Backer muscular dystrophy deletion carriers and normal females. Mol. Cell. Probes 10, 129–137, 1996.*

Liang et al., Recent advances in differential display. Current Opinion in Immunology 7, 274–280, 1995.*

Guo et al., Direct fluorescence analysis of genetic polymorphisms by hybridization with oligonucleotide arrays on glass supports. Nucleic Acids Res. 22, 5456–5465, 1994.*

Stephens et al., Transcriptional repression of the GLUT4 and C/EBP gene s in 3T3–L1 adipocytes by tumor necrosis factor–alpha . J. Biol. Chem. 266, 21839–21845, 1991.*

Smith et al., Automated differential display using a fluorescently labeled universal primer. Biotechniques 23, 274–279, Aug. 1997.*

* cited by examiner

Primary Examiner—Kenneth R. Horlick
Assistant Examiner—Frank Lu
(74) Attorney, Agent, or Firm—Sughrue Mion, PLLC (57) ABSTRACT

A plurality of cDNAs each having a known different base sequence are labeled with a fluorescent dye (FITC), whereby F-cDNA is prepared. The F-cDNA is disposed at a plurality of predetermined positions on the slide glass of a DNA micro array chip. Cy5-cDNA is prepared by synthesizing cDNA from poly(A)-mRNA in the presence of a fluorescent dye (Cy5). The Cy5-cDNA is placed on the DNA micro array chip and hybridized to the F-cDNA. After hybridization, the DNA micro array chip is read by a quantitative apparatus incorporated with an analyzer in which information about the base composition ratio and base length of cDNA has been registered.

12 Claims, 5 Drawing Sheets

TEST PIECE AND QUANTITATIVE METHOD AND APPARATUS FOR AN ORGANISM-ORIENTED SUBSTANCE

BACKGROUND OF THE INVENTION

1. Field of the Invention

This invention relates to a test piece that is employed in deoxyribonucleic acid (DNA) analysis and immunological analysis and to a method and apparatus for measuring the quantity of an organism-originated substance using the test piece.

2. Description of the Related Art

It is now considered possible that the human genome project for determining and analyzing all the base sequences of a human genome as huge as about 3000 Mbp will be completed sooner than the original scheduled date and determined by 2003, and the focus of the human genome project is now shifting from systematic base sequence determination to systematic function analysis.

The specific content of generic information comes down to what protein is synthesized and under what condition. With respect to the former, i.e., what protein is synthesized, methods of analysis, such as Western blotting, Northern blotting, and Southern blotting, are hitherto well known. These methods can analyze what a specific protein, DNA, and ribonucleic acid (RNA) sampled are, but are not necessarily suitable for analyzing all proteins, DNA, and RNA, extracted from a cell, at the same time.

On the other hand, regarding the latter, i.e., under what conditions protein is synthesized, the conventional methods of analysis cannot perform sufficient analysis, because protein is controlled at a transfer level. The main reason for this is that control data of both the base sequence in DNA and the corresponding contents are insufficient.

However, with the latest advancements in techniques for fixing arbitrary oligonucleotide with high density on the surface of a 1-centimeter-square carrier called a DNA chip or a DNA micro array chip, it is expected that the analysis of gene expression information will increasingly advance. The DNA chip is formed by dividing a silicon chip into a plurality of sections using photolithography and directly synthesizing single-stranded DNA having a specific base sequence on each section. As to the DNA micro array chip, a DNA macro array chip having a spot size of about $300\mu$ or more previously blotted on the membrane is reduced to a spot size of about $200\mu$ or less and blotted on a slide glass. The DNA chip or the DNA micro array chip is connected to a signal reader and a computer system, and it can be known which probe DNA is hybridized by the DNA disposed on the chip or the micro array chip. Depending on the DNA type disposed on the DNA chip or the DNA micro array chip and the disposition, it is possible to employ the chip or the array chip in various analyses such as DNA mutation analysis, DNA polymorphism analysis, DNA base sequence analysis, and DNA expression analysis.

Figure 4A:
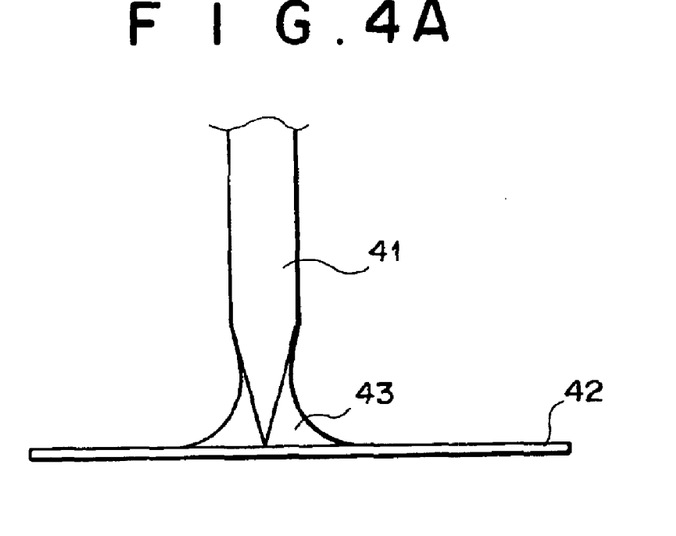
FIG. 4A is a side view showing how cDNA is disposed on a slide glass by a pin in direct contact with the slide glass.
Figure 4B:
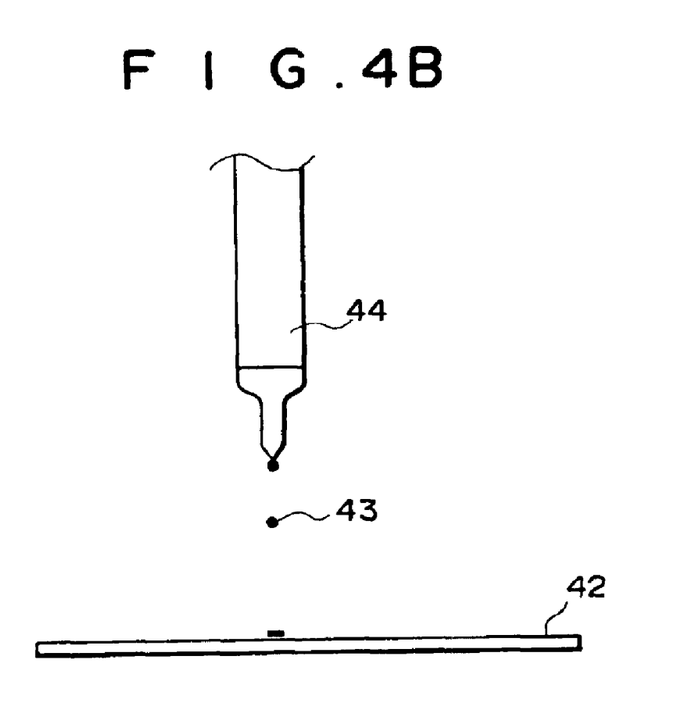
FIG. 4B is a side view showing how cDNA is blotted on the slide glass by a syringe in non-contact with the slide glass.
Figure 5:
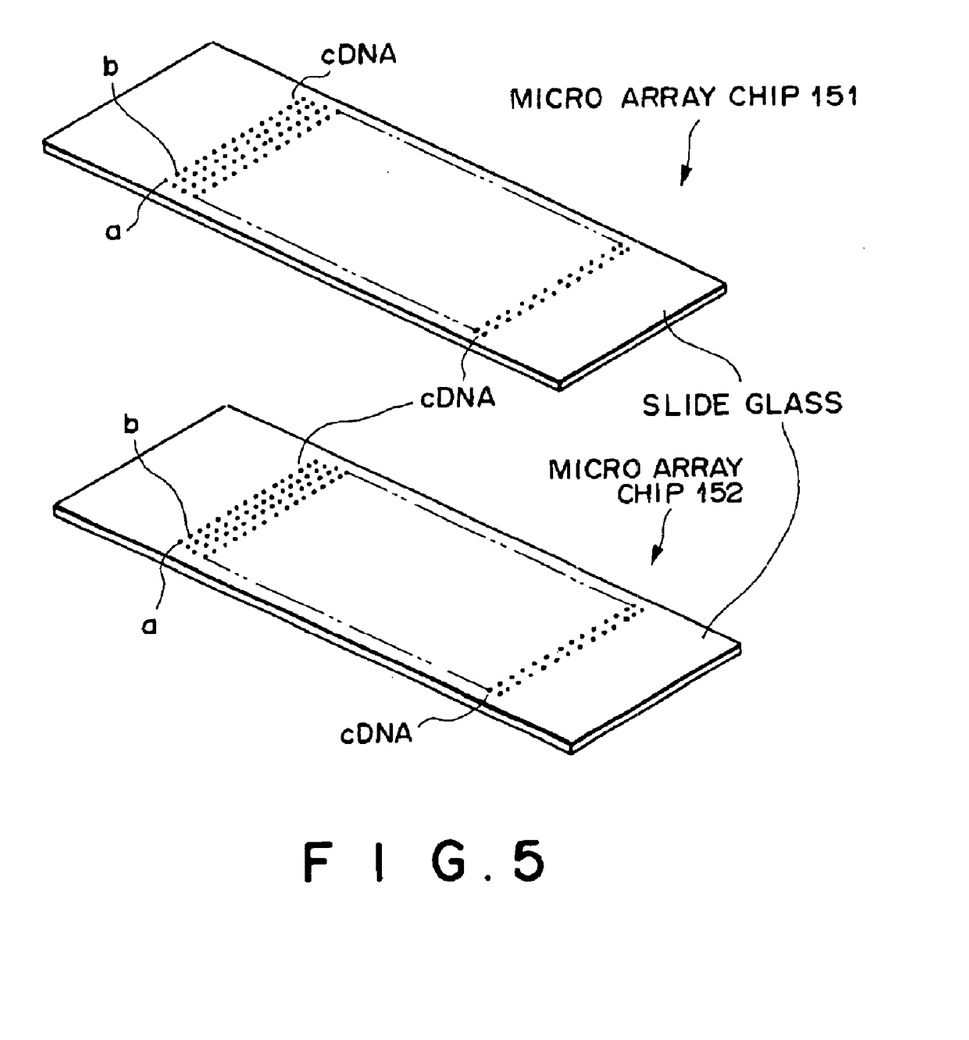
FIG. 5 is a perspective view of conventional DNA micro array chips.

The analysis employing the DNA micro array chip, however, still has quite a number of problems because discussions about array chip generation and a detector thereof have only just started. For instance, the micro array chip is made by blotting complementary DNA (cDNA) by means of a spotter, and as a method of generating the micro array chip, there is a contact printing method and a non-contact printing method. In the contact printing method, cDNA 43 is disposed on a slide glass 42 by a pin 41 in direct contact with the slide glass 42, as shown in FIG. 4A. In the non-contact printing method, cDNA 43 is blotted on the slide glass 42 by a syringe 44 in non-contact with the slide glass 42, as shown in FIG. 4B. In both the printing methods, however, there is a difference in quantity between blotted spots. Even in the best case, there is a quantity difference of 5 to 10% CV for the contact printing method and a quantity difference of 3 to 5% CV for the non-contact printing method. Further, there are sometimes defect spots and spoiled spots. For this reason, DNA varies in quantity between spots a and b on a DNA micro array chip 151, as shown in FIG. 5. DNA also varies in quantity between spot a on the DNA micro array chip 51 and spot a on a DNA micro array chip 152 generated in the same way. Because of this difference in quantity, there is a problem that the quantitative analysis of different DNAs generated from a single cell and the quantitative comparison of DNAs in the same cell differing in quantity of expression at a different time will actually include a considerable error.

To solve this problem, an improvement in the spotter was initially considered, but improvements to enhance the reproducibility of the quantity of a sample to be spotted are considered to have limits.

SUMMARY OF THE INVENTION

The present invention has been made in view of the aforementioned circumstances. Accordingly, it is the object of the present invention to provide a test piece, such as a DNA micro array chip, which is capable of performing accurate quantitative analysis even when there is a difference in quantity between blotted spots, without relying on an improvement in a spotter which enhances the reproducibility of the blotted spots.

To achieve the aforementioned object of the present invention and in accordance with one aspect of the present invention, there is provided a test piece for analyzing an organism-originated substance labeled with a second labeling substance. The test piece comprises a carrier on which a plurality of known specific binding substances differing from one another are disposed at a plurality of predetermined positions. The specific binding substances are labeled with a first labeling substance.

Since a plurality of known specific binding substances differing from one another are disposed at a plurality of predetermined positions on a carrier and labeled with a labeling substance, the quantity of a specific binding substance disposed on the test piece can be specified regardless of a difference in quantity between the specific binding substances that is caused when they are disposed on the carrier.

In accordance with another aspect of the present invention, there is provided a quantitative method comprising the steps of:

detecting a level of a first labeling signal emitted by a first labeling substance, which labels a plurality of known different specific binding substances respectively disposed at a plurality of predetermined positions on a carrier of a test piece, for each of the plurality of predetermined positions;

binding an organism-originated substance, labeled with a second labeling substance differing from the first labeling substance, to the specific binding substance and detecting a level of a second labeling signal emitted from the second labeling substance for each of the plurality of predetermined positions; and measuring a quantity of the organism-originated substance bound to the specific binding substance, based on the detected level of the first labeling signal and the detected level of the second labeling signal.

In accordance with still another aspect of the present invention, there is provided a quantitative apparatus comprising:

first detection means for detecting a level of a first labeling signal emitted by a first labeling substance, which labels a plurality of known different specific binding substances respectively disposed at a plurality of predetermined positions on a carrier of a test piece, for each of the plurality of predetermined positions;

second detection means for detecting a level of a second labeling signal emitted by a second labeling substance, which differs from the first labeling substance and labels an organism-originated substance bound to the specific binding substance, for each of the plurality of predetermined positions; and analyzing means for measuring a level of the organism-originated substance bound to the specific binding substance, based on the detected level of the first labeling signal and the detected level of the second labeling signal.

According to the quantitative method and the quantitative apparatus of the present invention, a level of a first labeling signal emitted by a first labeling substance, which labels a plurality of known different specific binding substances respectively disposed at a plurality of predetermined positions on a carrier of a test piece, is detected for each of the plurality of predetermined positions. An organism-originated substance, labeled with a second labeling substance differing from the first labeling substance, is bound to the specific binding substance and a level of a second labeling signal emitted by the second labeling substance is detected for each of the plurality of predetermined positions. Also, a quantity of the organism-originated substance bound to the specific binding substance is measured based on the detected level of the first labeling signal and the detected level of the second labeling signal. Therefore, it is possible to measure the quantity of the organism-originated substance independently of a difference in quantity between the specific binding substances. In addition, it becomes possible to read out the specific binding substance and the organism-originated substance disposed on the same test piece at the same time, because the labeling substance for the organism-originated substance differs from the labeling substance for the specific binding substance.

Note that if the test piece, the quantitative method, and the quantitative apparatus of the present invention are employed, an effective selection of medicine and wide utilization such as functional analysis of EST will become possible, for example, by measuring various proteins manifested according to the growth of a cancer, with the explication of the control contents and mechanism of protein synthesis being controlled at a transfer level or the realization of the measurement of a specific protein synthesized in the process of a disease, obtained from messenger RNA (mRNA) transferred within a cell.

The "carrier" may be any type if a specific binding substance can be stably bound and spotted. For example, the carrier may be a membrane filter, a slide glass plate, etc. These carriers may be preprocessed to stably bind a specific binding substance.

The "specific binding substance" means a substance bindable specifically with an organism-originated substance, such as hormones, a tumor marker, enzyme, an antibody, an antigen, abzyme, the other proteins, a nucleic acid, cDNA, DNA, RNA and the like. The "known" varies depending on the specific binding substance. For example, in the case of a nucleic acid, the "known" means that the base sequence and the base length are known, and in the case of protein, it means that the composition of the amino acid is known. Here, the specific binding substances disposed at predetermined positions on the carrier means that one kind of specific binding substance has been disposed for each position.

The "organism-originated substance" is a substance that specifically binds with a known specific binding substance disposed at a predetermined position on the carrier, and means, for example, substances extracted, isolated and the like from a living organism. The "organism-originated substance" includes substances extracted directly from a living organism and also includes these substances chemically processed and chemically modified. For instance, the "organism-originated substance" includes hormones, a tumor marker, enzyme, an antibody, an antigen, abzyme, the other proteins, a nucleic acid, cDNA, DNA, RNA and the like.

The specific binding substance labeled with a labeling substance (also referred to simply as a labeled specific binding substance) may be labeled at one point such as one end of stranded molecules or at a few points. If the specific binding substance has been labeled at one point, the quantity of the specific binding substance disposed at each position on the carrier is usually detectable. In the case where enhancement of detection sensitivity is desired or in the case where it is technically difficult or becomes technically complicated to label the specific binding substance at one point, the specific binding substance may be labeled at a few points.

It is preferable that the labeling substance for the organism-originated substance is different from the labeling substance for the specific binding substance. The reason for this is that a labeling signal from the labeling substance for the organism-originated substance and a labeling signal from the labeling substance for the specific binding substance can be detected independently of each other at the same time. The labeling substance for the organism-originated substance may label the organism-originated substance at one point or at a few points; although one point is preferred. The reason for this is that in the case of the organism-originated substance, there are cases where its component is not known and therefore confirmation of a method of taking a labeling substance into the organism-originated substance becomes necessary and technically complicated. Note that in the case of a known labeling substance, the organism-originated substance may be labeled at a few points similarly to the specific binding substance.

The "labeling substance" means a marker substance that changes either a portion of the specific binding substance or a portion of the organism-originated substance, or is added directly to these substances, in order to obtain information from these substance. The labeling substance is not particularly limited, as long as a detection signal emitted therefrom can be detected and also a rule that the labeling substance is taken into either the specific binding substance or the organism-originated substance is known in advance. For example, it is preferable to employ a fluorescent dye such as SYBR Green II™, Cy5™, fluorescein isothiocyanate and the like, or a radioactive isotope such as $^{32}P$, $^{33}P$ and the like. The "labeling signal" means one emitted or output from a labeling substance. For example, the labeling signal means fluorescent light when the labeling substance is a fluorescent dye and radiation when the labeling substance is a radioactive isotope. In this case, a radioactive isotope may be employed in a specific binding substance and a fluorescent dye in an organism-originated substance, or a fluorescent dye may be employed in a specific binding substance and a radioactive isotope in an organism-originated substance. Furthermore, fluorescent dyes may be employed in both a specific binding substance and an organism-originated substance. Note that in the case where fluorescent dyes are employed in both a specific binding substance and an organism-originated substance, it is necessary to employ fluorescent dyes whose fluorescent wavelength bands do not overlap with each other. When they overlap, it is necessary to employ fluorescent dyes that do not overlap at at least a major band of detection. On the other hand, when a radioactive isotope is employed, a specific binding substance on a carrier labeled with the radioactive isotope is contacted with a photostimulable phosphor sheet and is exposed and the sheet is read by a laser, as disclosed in Japanese Patent Publication No. 5(1993)-20712 (automatic radiography of measuring a quantity of a radioactive isotope). The "rule that a labeling substance is taken into either a specific binding substance or an organism-originated substance is known in advance" means that when the labeling substance is SYBR Green II™, for example, there is a rule that it is weakly bound to single-stranded DNA or RNA and absorbed in accordance with the base length. Also, when the labeling substance is Cy5-nucleotide, there is a rule that it is taken randomly or into an end of DNA or RNA. On the other hand, a radioactive isotope such as $^{32}P$ varies depending on a substance that is labeled by the radioactive isotope. For instance, when dNTP[$\alpha$-$^{32}P$], which is employed as substrates in synthesizing cDNA from mRNA, is used, there is a rule that $^{32}P$ is randomly incorporated and the amount of $^{32}P$ is in proportion to the base included in the labeled nucleotide.

The "binding an organism-originated substance to the specific binding substances" means a case (hybridization) such that a stable double strand, as is viewed in DNA or RNA, is formed between complementary nucleotides and also means an extremely high specificity bond that selectively reacts only to a specific substance, such as a bond between an antigen and an antibody, a bond between biotin and avidin and the like.

The "measuring a quantity of the organism-originated substance bound to the specific binding substance, based on the detected level of the first labeling signal and the detected level of the second labeling signal" means that because the level of the first labeling signal emitted from the first labeling substance of the specific binding substance at one position on the carrier is proportional to the quantity of the specific binding substance disposed at that position, the level of the second labeling signal of the second labeling substance of the organism-originated substance bound to the specific binding substance is caused to correspond to the level of the first labeling signal, and therefore the quantity (density) of the organism-originated substance can be measured regardless of a difference in quantity between the specific binding substances. For example, consider the case where the specific binding substance is cDNA. Assume that when the number of cDNAs (specific binding substances) with one end labeled with a fluorescent dye is a at the nth position on the carrier, the quantity of fluorescent light (quantity of a labeling signal emitted from a labeling substance) is Ps. On the other hand, the number of probe DNAs (organism-oriented substances) with one end of one molecule labeled with a fluorescent dye is assumed to be c.

Furthermore, assume that when the probe DNA and the nth cDNA are hybridized, the quantity of fluorescent light is PC. It has been said that in a liquid phase system, probe DNA which is hybridized with cDNA depends on cDNA and conditions, but is about 1/100. Although it cannot be said that the case of the carrier is a perfect liquid phase system, the density m of the probe DNA is proportional at least to the number of cDNAS existing at the nth position, a. Therefore, Pc is proportional to Pc and m and the following relationship is established.

$$Pc \propto mPs$$

Therefore, if Ps and Pc are measured, the density m of the organism-originated substance bound at the nth position will be obtained.

In the case where cDNA is labeled at one point, the value of Ps has no relation to the base sequence and base length of cDNA and is proportional only to the number of cDNAs disposed at the nth position. However, in the case where a labeling substance labels a specific base or labels a few points (in certain cases, tens of points) per one molecule of cDNA, the quantity of fluorescent light is varied even by the base length, and consequently, even if all the positions on a sheet of carrier indicate the same quantity of fluorescent light, it cannot be said that cDNA of the same quantity has been blotted at all the positions, because the bases of cDNA vary in length. Therefore, in this case, there is a further need to calculate "a characteristic value related to cDNA". That is, a characteristic value related to cDNA, such as the base composition ratio and base length of cDNA disposed on the carrier, a quantity of fluorescent light when N cDNAs are included at one position on a carrier and the like, needs to be registered in a computer for each position. What characteristic value becomes necessary varies depending on a labeling substance employed. The fluorescence quantity Pc of probe DNA is proportional to the density m of probe cDNA and the fluorescent quantity Ps of cDNA and inversely proportional to the number of labeling substances labeling single-stranded cDNA. Therefore, the density m of probe DNA is represented by the following equation, and a characteristic value that can calculate the number of labeling substances labeling single-stranded (1 molecule) cDNA becomes necessary.

$m \propto Pc/Ps \times$(number of a labeling substance labeling single-stranded cDNA)

For instance, in the case of labeling one of the 4 bases of cDNA, the number of labeled specific bases included in 1-molecule cDNA becomes necessary as a characteristic value. In the case where a labeling substance is proportional to the length of a base, the base length and the base rate at which 1 labeling substance is incorporated (i.e., how many of every of the bases 1 labeling substance is absorbed) become necessary as characteristic values.

The above and many other objects, features and advantages of the present invention will become manifest to those skilled in the art upon making reference to the following detailed description and accompanying drawings in which preferred embodiments incorporating the principle of the present invention are shown by way of illustrative example.

BRIEF DESCRIPTION OF THE DRWAINGS

DESCRIPTION OF THE PREFERRED EMBODIMENTS

Figure 1:
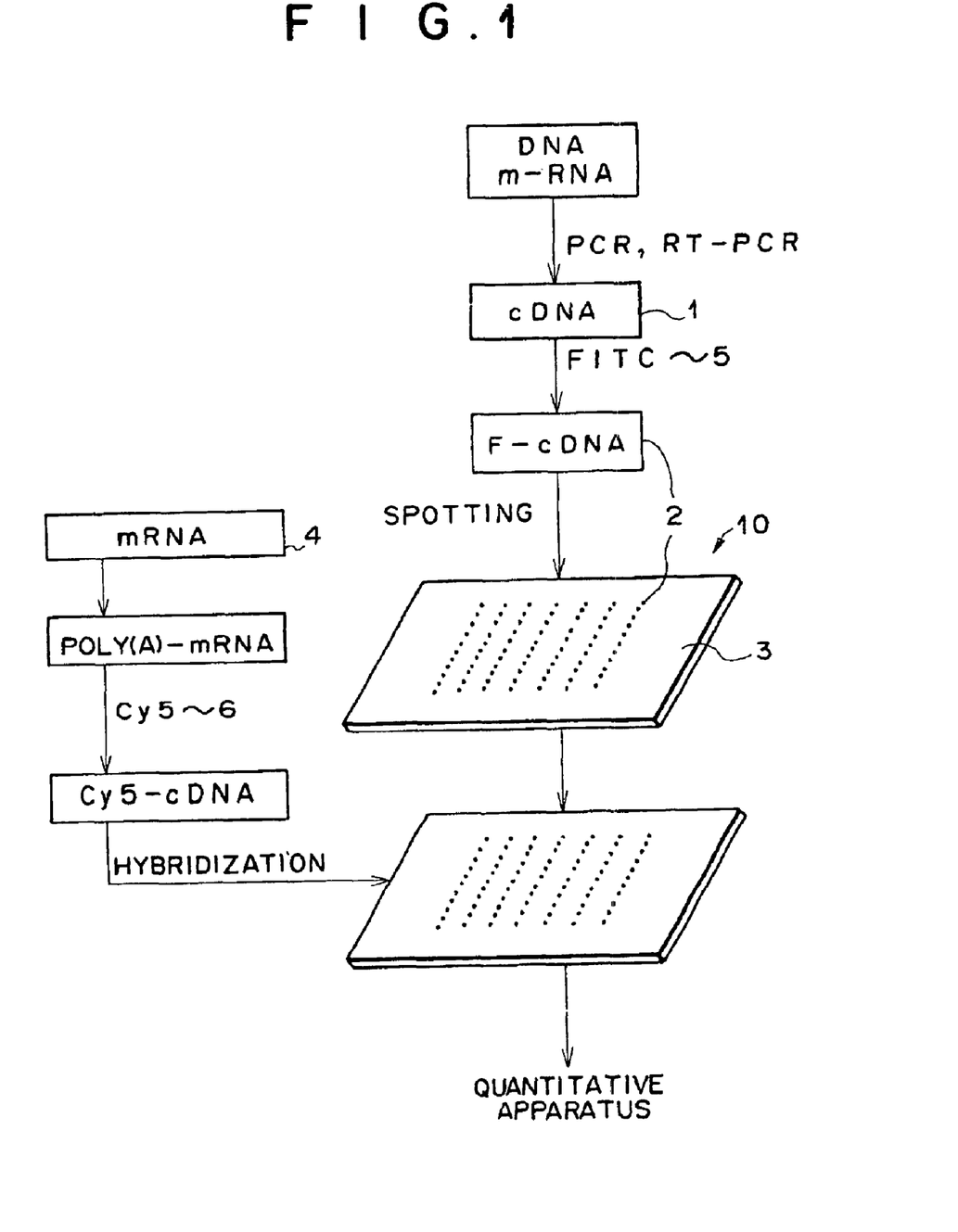
FIG. 1 is a flowchart showing how a test piece according to an embodiment of the present invention is made.

Referring to FIG. 1, there is shown a preferred embodiment of a test piece in accordance with the present invention. In the preferred embodiment, a DNA micro array chip is used as an example of the test piece and cDNA is used as an example of a specific binding substance. Furthermore, mRNA extracted from a cell is used as an example of an organism-originated substance.

In a DNA micro array chip 10 according to the preferred embodiment, a plurality of different cDNAs 1 (specific binding substances) each having a known base sequence are labeled with a fluorescent dye 5 (e.g., fluorescein isothiocyanate (hereinafter referred to as FITC)) and are disposed at predetermined positions on a slide glass (carrier) 3. The surface of the slide glass 3 is preprocessed with a poly-N-lysine solution, and the fluorescent dye 5 is a labeling substance which labels a specific binding substance.

The cDNA 1 is prepared from known DNA, mRNA and the like using a PCR method or a RT-PCR method. At this time, if deoxycytidine 5'-triphosphate (dCTP) labeled with the FITC 5 is employed, the position of cytosine (C) of the 4 bases of DNA is labeled with the FITC 5, whereby F-cDNA (labeled specific binding substance) 2 can be prepared. The prepared F-cDNA 2 is spotted at predetermined positions on the slide glass 3 by a spotter, thus making the DNA micro array chip 10.

On the other hand, mRNA (organism-originated substance) 4 to be measured is extracted from a cell, and poly(A)-mRNA having a polyadenylic acid (poly(A)) tail at its 3' end is extracted from mRNA 4. If cDNA is synthesized from poly(A)-mRNA in the presence of Cy5-dUTP (e.g., Cy5 which labels an organism-originated substance), Cy5-cDNA (probe DNA) is made. Of course, it is possible to label the end by use of a labeling primer.

The Cy5-cDNA is prepared in a predetermined solution and is slowly placed on the DNA micro array chip 10 to perform normal hybridization.

Figure 2:
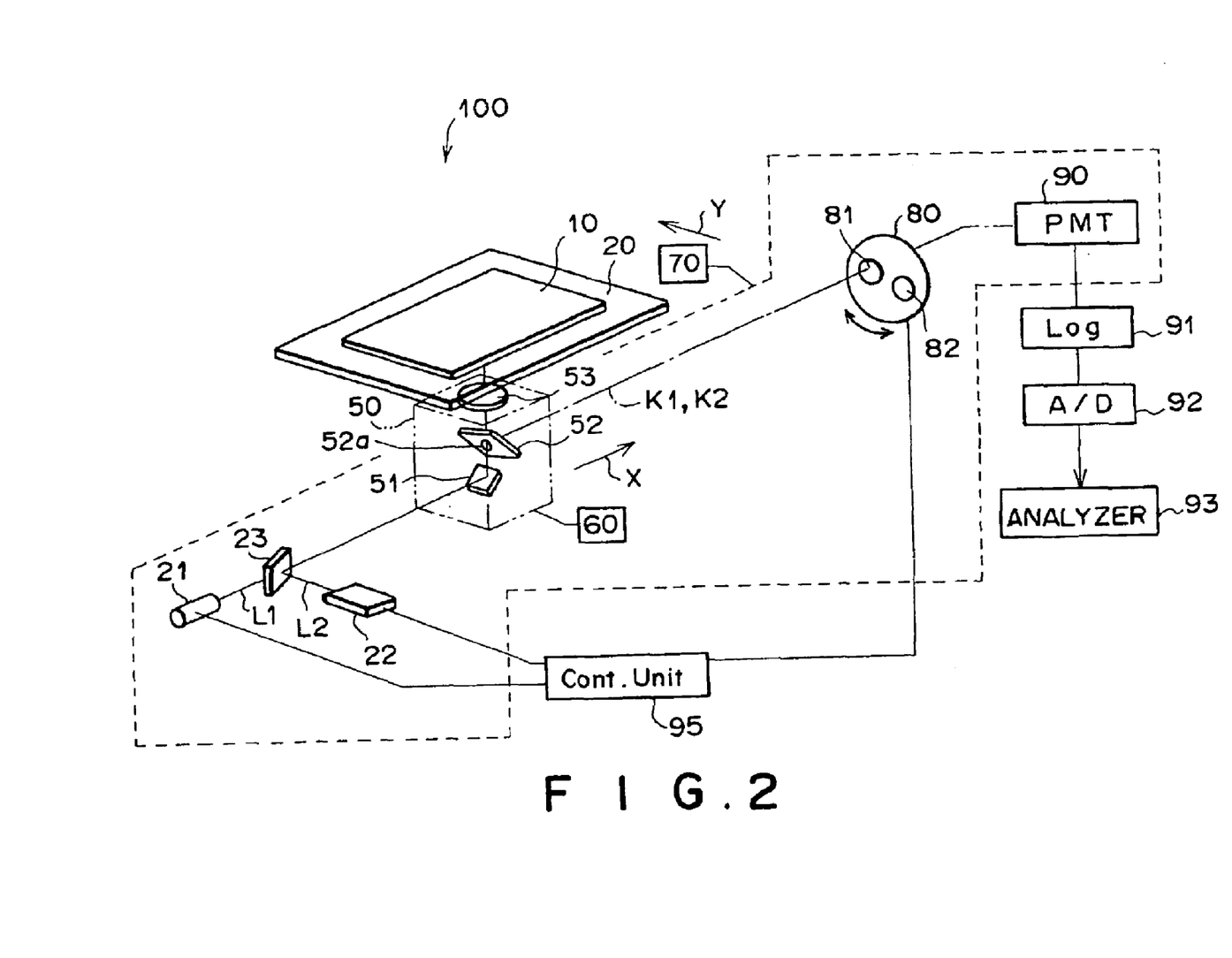
FIG. 2 is a schematic diagram showing an embodiment of a quantitative apparatus of the present invention.

Now, with reference to FIG. 2, a description will be given of a quantitative apparatus 100 that measures the Cy5-cDNA hybridized on the DNA micro array chip 10 shown in FIG. 1. The quantitative apparatus 100 includes (1) a sample tray 20 on which the DNA micro array chip 10 distributing the F-cDNA 2 labeled with the FITC 5 is placed at a predetermined position; (2) an argon (Ar) laser (excitation wavelength 488 nm) or a SHG laser (excitation wavelength 473 nm) 21 which emits laser light L1 of luminescence wavelength suitable for exciting the fluorescent dye (FITC) 5; (3) a He-Ne laser (excitation wavelength 633 nm) or a semiconductor laser (excitation wavelength 635 nm) 22 which emits laser light L2 of luminescence wavelength suitable for exciting the fluorescent dye (Cy5) 6; (4) a first dichroic mirror 23 which transmits the first laser light L1 therethrough and reflects the second laser light L2; (5) a photomultiplier (hereinafter referred to as a PMT) 90 which photoelectrically detects fluorescent light emitted from the fluorescent dyes 5, 6 on the DNA micro array chip 10 excited by the first laser light L1 and the second laser light L2; (6) an optical head 50 which directs the first laser light L1 and the second laser light L2 emitted from the first and second lasers 21, 22 to the DNA micro array chip 10 placed on the sample tray 20 and also guides the fluorescent light emitted from the DNA micro array chip 10 to the PMT 90; (7) a filter set 80 with two kinds of switchable band-pass filters 81, 82 disposed in the optical path between the optical head 50 and the PMT 90; (8) horizontal scanning means 60 which moves the optical head 50 at uniform speed in the direction of arrow X; (9) vertical scanning means 70 which moves the lasers 21, 22, the optical head 50, the filter set 80, and the PMT 90 as one body in the direction of arrow Y perpendicular to the direction of arrow X; (10) an amplifier 91 which logarithmically amplifies a detection signal detected by the PMT 90; (11) an A/D converter 92 which converts the amplified detection signal to a digital signal; (12) an analyzer 93 which analyzes the digital signal by comparing the digital signal with the previously input data on the DNA micro array chip 110; and (13) a control unit 95 which controls emission of the first laser light L1 and the second laser light L2 and also controls the filter set 80 so that either the band-pass filter 81 or the band-pass filter 82 is disposed in the above-mentioned optical path.

Next, a description will be given of the operation of the quantitative apparatus 100 of the preferred embodiment.

The DNA micro array chip 10, which includes the F-cDNA 2 labeled with the FITC 5 and the Cy5-cDNA hybridized to the F-cDNA 2, is first placed on the sample tray 20. The control unit 95 controls the first and second lasers 21, 22 so that the first laser light L1 and the second laser light L2 are selected and emitted. As a result of this control, the first laser 21 emits the first laser light L1, while the second laser 22 emits the second laser light L2. The control unit 95 also controls the filter set 80 so that the first filter 81 is disposed in the optical path between the optical head 50 and the PMT 90. In this way, the filter set 80 places the first filter 81 in the optical path.

The first laser light L1 emitted from the first laser 21 is transmitted through the dichroic mirror 23 and travels in the direction of arrow X. The first laser light L1 incident on the plane mirror 51 of the optical head 50 is reflected upward. The reflected light beam L1 passes through the aperture 52a of an aperture mirror 52 and is incident on a lens 53. A small area on the DNA micro array chip 10 placed on the sample tray 20 is irradiated with the first laser light L1. On the other hand, the optical head 50 is being moved at high and uniform speed in the direction of arrow X by the horizontal scanning means 60, so that the first laser light L1 scans the DNA micro array chip 10 in the direction of arrow X. During this horizontal scanning, for the F-cDNA 2 on the small area irradiated with the first laser L1, the FITC 5 is excited by the first laser light L1 and emits fluorescent light K1.

The fluorescent light K1 emitted by the first laser light L1 spreads in all directions from the lower surface of the DNA micro array chip 10 and is formed into a downward fluorescent light beam K1 by the lens 53 of the optical head 50. The fluorescent light beam K1 is reflected by the reflecting surface of the aperture mirror 52 and travels in the direction of arrow X. The first band-pass filter 81 prevents the passage of light other than the fluorescent light beam K1, so only the fluorescent light beam K1 traveling in the direction of arrow X is incident on the PMT 90. The fluorescent light beam K1 incident on the PMT 90 is amplified and photoelectrically detected as a corresponding electrical signal by the PMT 90. The electrical signal is amplified by the logarithmic amplifier 91 and is converted to a digital signal by the A/D converter 92. The digital signal is output to the analyzer 93.

If single horizontal scanning ends in this manner, the optical head 50 is returned to the original position by the horizontal scanning means 60. While the optical head 50 is being returned to the original position, the vertical scanning means 70 moves the lasers 21, 22, the optical head 50, the filter set 80, and the PMT 90 as one body in the direction of arrow Y. By reiterating the horizontal scanning and the vertical scanning, the entire surface of the DNA micro array chip 10 is irradiated with the first laser light L1, and the fluorescent light beam K1 corresponding to each position on the DNA micro array chip 10 is acquired as a digital signal.

If the data of the fluorescent light beam K1 is acquired up to the last position on the DNA micro array chip 10 by the horizontal scanning and the vertical scanning, the optical head 50 is returned to the initial position. Similarly, a fluorescent light beam K2 is emitted from the DNA micro array chip 10 irradiated with the second laser light L2 emitted from the second laser 22 and is incident on the PTM 90 by the second band-pass filter 82 which prevents the passage of light other than the fluorescent light beam K2. Next, the fluorescent light beam K2 is digitized and acquired by repeating the horizontal scanning and the vertical scanning in the same way as the above-mentioned fluorescent light beam K1. In this embodiment, although the fluorescent light beam K1 is first read out for all the positions on the DNA micro array chip 10 and then the fluorescent light beam K2 is read out, the operation of first emitting the first laser light L1 to read out the fluorescent light K1 and then emitting the second laser light L2 to the same position to read out the fluorescent light K2 may be repeated for all the positions on the DNA micro chip array 10.

Figure 3:
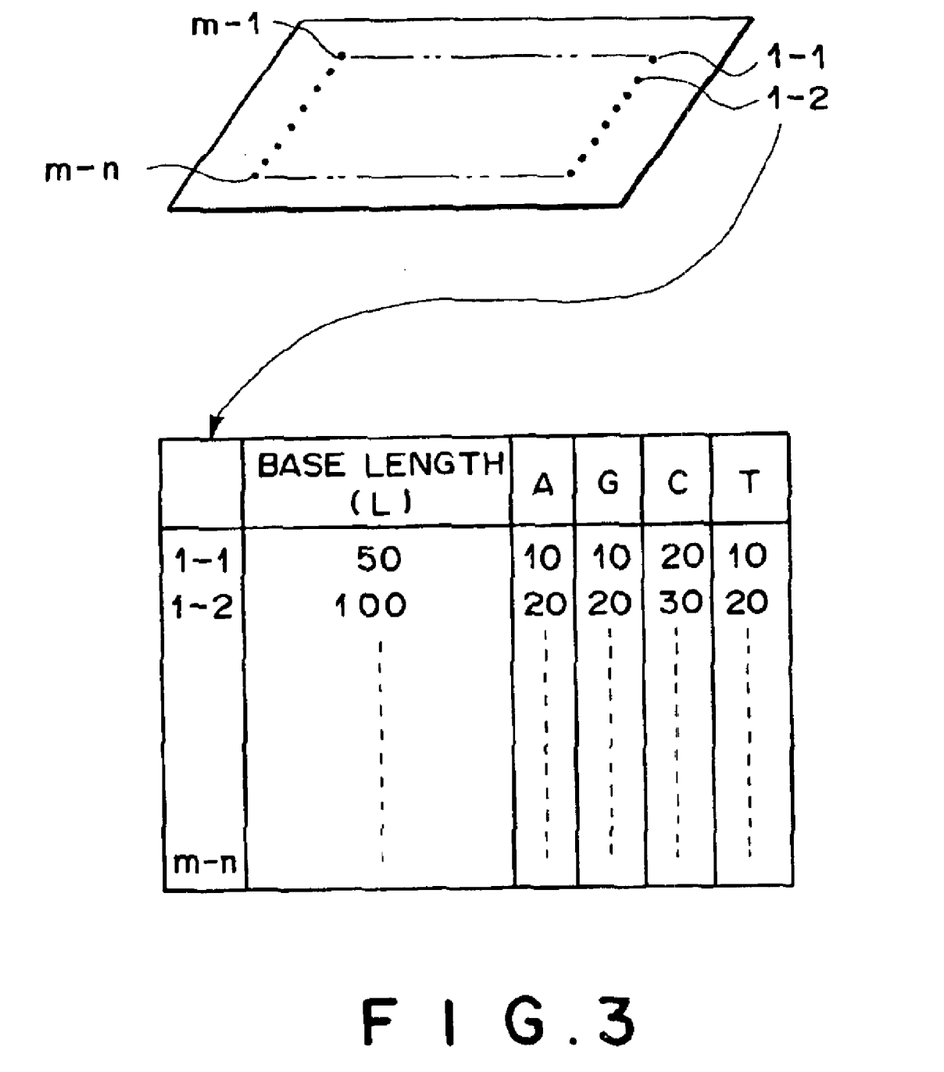
FIG. 3 is a diagram showing data held in the quantitative apparatus of the present invention.

As shown in FIG. 3, the data of the base composition ratio (adenine (A), guanine (G), cytosine (C), thymine (T)) per single-stranded F-cDNA disposed at each position on the DNA micro array chip 10 has been registered in the analyzer 93 that has acquired the digital signal corresponding to each position on the DNA micro array chip 10. Therefore, the density of Cy5-cDNA at each position can be calculated from the registered data of the base composition ratio per single-stranded F-cDNA, the registered data of the fluorescent light quantity of F-cDNA, the measured fluorescent light quantity of F-cDNA, and the measured fluorescent light quantity of Cy5-cDNA. For instance, if the fluorescent light quantity of F-cDNA at the (1—1)st position is assumed to be $P_1$ and the fluorescent light quantity of Cy5-cDNA at the (1—1)st position is assumed to be $P_2$, the density m of Cy5-cDNA will become m OC $P_1/P_1 \times 20$. If analysis is likewise performed for all the positions on the DNA micro array chip 10, the density of Cy5-cDNA at each position will be obtained.

In the preferred embodiment, although FITC and Cy5 have been employed as fluorescent dyes, it is also possible to employ the other fluorescent dyes and radio isotopes. In this case, if the known base length and base composition ratio of cDNA and the known fluorescent light or radiation quantity of cDNA at each position have been registered according to a labeling substance in the analyzer 93, calculating the density of probe DNA at each position will be possible by measuring either the fluorescent light or radiation quantity of cDNA on a newly made DNA micro array chip and measuring either the fluorescent light or radiation quantity of probe DNA.

While the present invention has been described with the DNA micro array chip as a test piece, cDNA as a specific binding substance, and mRNA extracted from a cell as an organism-originated substance, the invention is not limited to this example, but may be modified within the scope of the appended claims.

What is claimed is:

1. An apparatus for measuring a value detected from a second label corrected for a value detected from a first label comprising:
   a test piece with a plurality of known different specific binding substances respectively disposed at a plurality of predetermined positions thereon, wherein said different specific binding substances are each labeled with a first labeling substance, wherein an organism-originated substance specifically binds to at least one of said specific binding substances, and wherein said organism-originated substance is labeled with a second labeling substance that differs from said first labeling substance;
   a first detection unit, wherein said first detection unit detects a level of a first labeling signal emitted by said first labeling substance;
   a second detection unit, wherein said second detection unit detects a level of a second labeling signal emitted by said second labeling substance; and
   an analyzing unit, wherein said analyzing unit measures a quantity of said organism-originated substance bound to each of said specific binding substances, based on a detected level of said second labeling signal, corrected for a detected level of said first labeling signal at each of said predetermined positions.

2. The apparatus as set forth in claim 1, wherein said specific binding substances are cDNA polynucleotides.

3. The apparatus as set forth in claim 1, wherein said analyzing unit utilizes a correction value calculated for each of said specific binding substances.

4. The apparatus as set forth in claim 1, wherein said first labeling substance is a fluorescent dye.

5. The apparatus as set forth in claim 2, wherein said first labeling substance is a fluorescent dye.

6. The apparatus as set forth in claim 3, wherein said first labeling substance is a fluorescent dye.

7. An apparatus for measuring a value detected from a second label corrected for a value detected from a first label comprising:
   a test piece with a plurality of known different specific binding substances respectively disposed at a plurality of predetermined positions thereon, wherein said different specific binding substances are cDNA polynucleotides and are each labeled with a first labeling substance, wherein an organism-originated substance specifically binds to at least one of said specific binding substances, and wherein said organism-originated substance is labeled with a second labeling substance that differs from said first labeling substance;
   a first detection, wherein said first detection unit detects a level of a first labeling signal emitted by said first labeling substance;
   a second detection unit, wherein said second detection unit detects a level of a second labeling signal emitted by a second labeling substance;
   an analyzing unit, wherein said analyzing unit measures a quantity of said organism-originated substance bound to each of said specific binding substances, based on the detected level of said second labeling signal, corrected for the detected level of said first labeling signal at each of said predetermined positions,
   wherein said analyzing unit utilizes a correction value calculated from 1) the length of each of said cDNA polynucleotides and 2) the relative frequency of said first labeling substance within each of said cDNA polynucleotides.

8. The apparatus as set forth in claim 7, wherein said first labeling substance is a fluorescent dye.

9. The apparatus as set forth in claim 1, wherein said first labeling substance is a radioactive isotope.

10. The apparatus as set forth in claim 2, wherein said first labeling substance is a radioactive isotope.

11. The apparatus as set forth in claim 3, wherein said first labeling substance is a radioactive isotope.

12. The apparatus as set forth in claim 7, wherein said first labeling substance is a radioactive isotope.

* * * * *